(12) United States Patent
Shashidhara et al.

(10) Patent No.: US 11,893,030 B2
(45) Date of Patent: Feb. 6, 2024

(54) SYSTEM AND METHOD FOR IMPROVED STATE IDENTIFICATION AND PREDICTION IN COMPUTERIZED QUERIES

(71) Applicant: CERNER INNOVATION, INC., Kansas City, KS (US)

(72) Inventors: Darshan Matada Shashidhara, Bangalore (IN); Amarrtya Jana, Kolkata (IN); Aiswarya Ramachandran, Bangalore (IN); Girish Sharavana, Bangalore (IN); Winston Rohan DSouza, Bengaluru (IN); Pratyush Kumar, Bangalore (IN)

(73) Assignee: Cerner Innovation, Inc., Kansas City, MO (US)

( * ) Notice: Subject to any disclaimer, the term of this patent is extended or adjusted under 35 U.S.C. 154(b) by 404 days.

(21) Appl. No.: 17/036,451

(22) Filed: Sep. 29, 2020

(65) Prior Publication Data
US 2022/0100769 A1 Mar. 31, 2022

(51) Int. Cl.
*G06F 16/00* (2019.01)
*G06F 16/2457* (2019.01)
*G06F 40/30* (2020.01)
*G06N 3/08* (2023.01)
*G06F 16/25* (2019.01)
*G06F 3/14* (2006.01)

(52) U.S. Cl.
CPC ...... *G06F 16/24578* (2019.01); *G06F 16/252* (2019.01); *G06F 40/30* (2020.01); *G06N 3/08* (2013.01); *G06F 3/14* (2013.01)

(58) Field of Classification Search
CPC .. G06F 16/24578; G06F 16/252; G06F 40/30; G06F 3/14; G06N 3/08
USPC ......................................................... 707/723
See application file for complete search history.

(56) References Cited

U.S. PATENT DOCUMENTS

| | | | |
|---|---|---|---|
| 9,058,580 B1 * | 6/2015 | Amtrup | G06Q 10/06316 |
| 10,268,646 B2 * | 4/2019 | Jaech | G06F 16/9535 |
| 2017/0116379 A1 * | 4/2017 | Scott | G16H 50/20 |
| 2017/0124474 A1 * | 5/2017 | Kashyap | G06N 20/00 |
| 2018/0052928 A1 * | 2/2018 | Liu | G06F 16/951 |
| 2018/0082197 A1 * | 3/2018 | Aravamudan | G06F 40/30 |
| 2018/0113781 A1 * | 4/2018 | Kim | G06F 11/3438 |
| 2019/0171792 A1 * | 6/2019 | Manica | G06F 40/216 |

(Continued)

FOREIGN PATENT DOCUMENTS

WO WO-2016165471 A1 * 10/2016 ............. H04L 41/00
WO WO-2021236702 A1 * 11/2021

*Primary Examiner* — Leslie Wong
(74) *Attorney, Agent, or Firm* — Invoke

(57) ABSTRACT

Methods, systems, and computer-readable media are disclosed herein for improved state identification and prediction in computerized queries. In an aspects, a neural network model is trained via word embedding, using a plurality of workflows having a plurality of steps as input training data. The model may be searched using a string to locate and identify semantic matches as potential results, where the potential results correspond to a specific step and/or a particular workflow. Markov chaining may also be performed, using the potential results, in order to predict one or more additional results, where the additional results correspond to a specific succeeding step within a particular workflow, in some aspects. The results and predicted steps may be displayed.

21 Claims, 16 Drawing Sheets

(56) References Cited

U.S. PATENT DOCUMENTS

| | | | |
|---|---|---|---|
| 2019/0339950 A1* | 11/2019 | Meyer | G06F 8/38 |
| 2020/0104313 A1* | 4/2020 | Jayaraman | G06F 16/3329 |
| 2020/0293887 A1* | 9/2020 | De Brouwer | G06K 9/627 |
| 2021/0174191 A1* | 6/2021 | Dube | G06N 3/08 |
| 2021/0264202 A1* | 8/2021 | Kalluri | G06F 9/3005 |
| 2021/0264251 A1* | 8/2021 | Kalluri | G06K 9/6223 |
| 2021/0334467 A1* | 10/2021 | Wan | G06N 3/0454 |
| 2021/0358604 A1* | 11/2021 | Kearney | G06N 3/0445 |
| 2021/0407520 A1* | 12/2021 | Neckermann | H04L 12/1831 |
| 2022/0083603 A1* | 3/2022 | Sisto | G06F 16/3329 |
| 2022/0092028 A1* | 3/2022 | Layton | G06F 16/164 |
| 2022/0180447 A1* | 6/2022 | Kearney | A61B 6/14 |

* cited by examiner

| NAME | WorkflowName | Work Step Description |
|---|---|---|
| Addman Hospital | Ambulatory -- Provider Office Visit | Patient is ready to be seen by provider |
| Addman Hospital | Ambulatory -- Provider Office Visit | Review chart from Ambulatory Workflow |
| Addman Hospital | Ambulatory -- Provider Office Visit | Review/update Allergies |
| Addman Hospital | Ambulatory -- Provider Office Visit | Review home medications, renew/refill medications, and complete Medication Reconciliation |
| Addman Hospital | Ambulatory -- Provider Office Visit | Review/update histories (Social, Family, Procedure, Pregnancy) |
| Addman Hospital | Ambulatory -- Provider Office Visit | Select "Create Note" and review/update documentation as necessary |
| Addman Hospital | Ambulatory -- Provider Office Visit | Is note complete? |
| Addman Hospital | Ambulatory -- Provider Office Visit | Select Save and complete note once able |

```
"_source": {
    "workstep_description": "Record Results",
    "workflow_name": "Ambulatory- Stradland- In Office Process",
    "name": "North Hospital",
    "Average_Word_Embedding_128D_10W_Workflow_Data": [
        -6.065489768981934,
        -1.1797113418579102,
        1.2954628467559814,
        -3.987182855606079,
        -3.489670753479004,
        1.4012959003448486,
        -2.051857948303223,
        4.038065433502197,
        -7.07954216003418,
        4.411410331726074,
        -0.672147274017334,
        5.245535850524902,
        7.261448860168457,
        -2.3263320922851562,
        -1.632859230041504,
        -1.4008028507232666,
        -5.20004653930664,
        4.672865867614746,
        2.190180778503418,
        -4.892000198364258,
        2.1008758544921875,
        -0.16489553451538086,
        -0.02128744125366211,
        -3.3390650749206543,
        1.9366860389709473,
        1.1722160577774048,
        0.6628320217132568,
        -1.79587721824646,
        -1.4382307529449463,
        -8.156302452087402,
        -0.083104193210 6018,
```

*FIG. 7.*

Select Type of Search: Client Workflow Search (Workflow)

Input Search Phrase: specimen collection failing

Client Filter: - ALL -   Status Filter: - ALL -   [Q Search]

✓ Success! Recommended Results!

* Total Workflows Mined: 28,709

| Workflow Results | JobAide Results |

Show [10 ▼] entries    Search: [    ]

| WorkflowName | Description | WorkflowStatus | Client | ProjectName | FacilityName |
|---|---|---|---|---|---|
| Search | Search | Search | Search | Search | Search |
| GA FS_Laboratory -- Specimen Management | Collect Now? Schedule? Locate/Identify Patient Order Entry Record Missed Collection Collection List ... | Approved | Regional Health System, Inc. | | |
| Laboratory -- Sample Management | Nurse Collect? Print Labels Record Missed Collection List Locate/Identify Patient Perform Collection ... | Approved | West Medical Center | | |

| Workflow Name | Similar Client | Similar Workflow | Similarity |
|---|---|---|---|
| BH_AL_CPM – Scheduling Ambulatory Appointment | St. Healthcare | FSV Scheduling with Foreign Registrati | 1.9319186 |
| BH_AL_CPM – Scheduling Ambulatory Appointment | Memorial Medical Center | Cancer Care – Schedule Appointment | 1.9299836 |
| BH_AL_CPM – Scheduling Ambulatory Appointment | ABC Health | Ambulatory – Reg/Scheduling Ofc. Visi | 1.9272892 |
| BH_AL_CPM – Scheduling Ambulatory Appointment | Medical Center, Inc | Central Scheduling | 1.9254102 |
| BH_AL_CPM – Scheduling Ambulatory Appointment | Care Health Services, Inc. | Patient Scheduling | 1.9225327 |
| BH_AL_CPM – Scheduling Ambulatory Appointment | National Medical Center | Oncology – Planned Inpatient Admissi | 1.9185513 |
| BH_AL_CPM – Scheduling Ambulatory Appointment | Memorial Health | STO – OPID MHFS | 1.9165734 |
| BH_AL_CPM – Scheduling Ambulatory Appointment | DEF HealthCare | Oncology – Schedule Appointment | 1.9164035 |
| BH_AL_CPM – Scheduling Ambulatory Appointment | Children's Hospital | S2_Ambulatory – Admin Before Visit | 1.9159812 |
| BH_AL_CPM – Scheduling Ambulatory Appointment | Health, Inc. | zCS_CPM – Schedule Appointment | 1.915021 |
| BH_AL_CPM – Scheduling Ambulatory Appointment | East Alabama Medical Center | CS_EAMC_Registration – PreRegistrati | 1.9134738 |
| BH_AL_CPM – Scheduling Ambulatory Appointment | Major Health Center | ESM – Schedule Appointment (Phase | 1.9132922 |
| BH_AL_CPM – Scheduling Ambulatory Appointment | General Health Center | Oncology_CS – Ambulatory - Before | 1.9126048 |
| BH_AL_CPM – Scheduling Ambulatory Appointment | University Hospital | CS_CPM – OP Visit Scheduling | 1.9123274 |
| BH_AL_CPM – Scheduling Ambulatory Appointment | West Medical | Medical Necessity Workflow | 1.912239 |
| BH_AL_CPM – Scheduling Ambulatory Appointment | Eastern Healthcare | Acute_CSR_ERM_Scheduling to PreP | 1.9106756 |
| BH_AL_CPM – Scheduling Ambulatory Appointment | Health Care Corporation | One Oncology – Before Visit | 1.9106702 |
| BH_AL_CPM – Scheduling Ambulatory Appointment | St. Healthcare | Scheduling to Orders with Sca | 1.910256 |

SYSTEM AND METHOD FOR IMPROVED STATE IDENTIFICATION AND PREDICTION IN COMPUTERIZED QUERIES

BACKGROUND

Data models may be created and trained using various input data and various techniques.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims as supported by the Specification, including the Detailed Description.

One aspect of the present disclosure relates to a method for improved state identification and prediction in computerized queries. In aspects, a model is generated through word embedding. The model is queried, in some aspects, using a string to identify semantic matches. In aspects, in response to querying the model, one or more results are identified that correspond to the semantic matches identified. Probabilities for the one or more results are determined, where the probabilities represent semantic strength of the semantic matches. In some aspects, the one or more results and the probabilities in a graphical user interface (GUI) are displayed in a ranked order.

In another aspect, the present disclosure relates to non-transitory computer-readable storage medium having instructions embodied thereon, the instructions being executable by one or more processors to perform a method for improved state identification and prediction in computerized queries. In aspects, the model is generated through word embedding. The model is searched using a query string to identify one or more semantic matches for the query string, in some aspects. In response to searching the model, a plurality of results are identified in the model, where the plurality of results correspond to semantic matches between the query string and one or more of a step or workflow in the model. Probabilities for the plurality of results are determined, where the probabilities represent semantic strength of the semantic matches. One or more additional results that are related to the plurality of results are predicted, in an aspect. Then, in aspects, the method causes a ranked display of the plurality of results identified, the probabilities determined, and the one or more additional results predicted, in a graphical user interface (GUI).

In yet another aspect, the present disclosure relates to a system for improved state identification and prediction in computerized queries. The system includes, in some aspects, one or more hardware processors that execute computer-readable instructions for a plurality of modules. In one aspect, the plurality of modules includes a training module that generates a model through word embedding. In some aspects, the plurality of modules includes a query module that searches the model using a query string to identify one or more semantic matches for the query string, and in response to searching the model, identifies a plurality of results in the model. The plurality of results correspond to semantic matches between the query string and one or more of a step or workflow in the model, in aspects. The query module, in an aspect, determines probabilities for the plurality of results that represent semantic strength of the semantic matches. In some aspects, a prediction module predicts one or more additional results that are related to the plurality of results. In further embodiments, a display module causes a ranked display of the plurality of results identified, the probabilities determined, and the one or more additional results predicted, in a graphical user interface (GUI).

BRIEF DESCRIPTION OF THE DRAWINGS

Illustrative aspects of the present invention are described in detail below with reference to the attached drawing figures, and wherein:

FIG. 5 depicts an example of structured data created from the raw data of FIG. 4, in accordance with aspects;

FIG. 7 depicts an example representation of computer programming code for training a neural network model, in accordance with aspects;

FIG. 10 depicts an example of a graphical user interface for presenting search results using the trained neural network model, in accordance with aspects;

FIG. 14 depicts an example of workflow and/or step similarity determinations across distinct entities, in accordance with some aspects;

DETAILED DESCRIPTION

Figure 1:
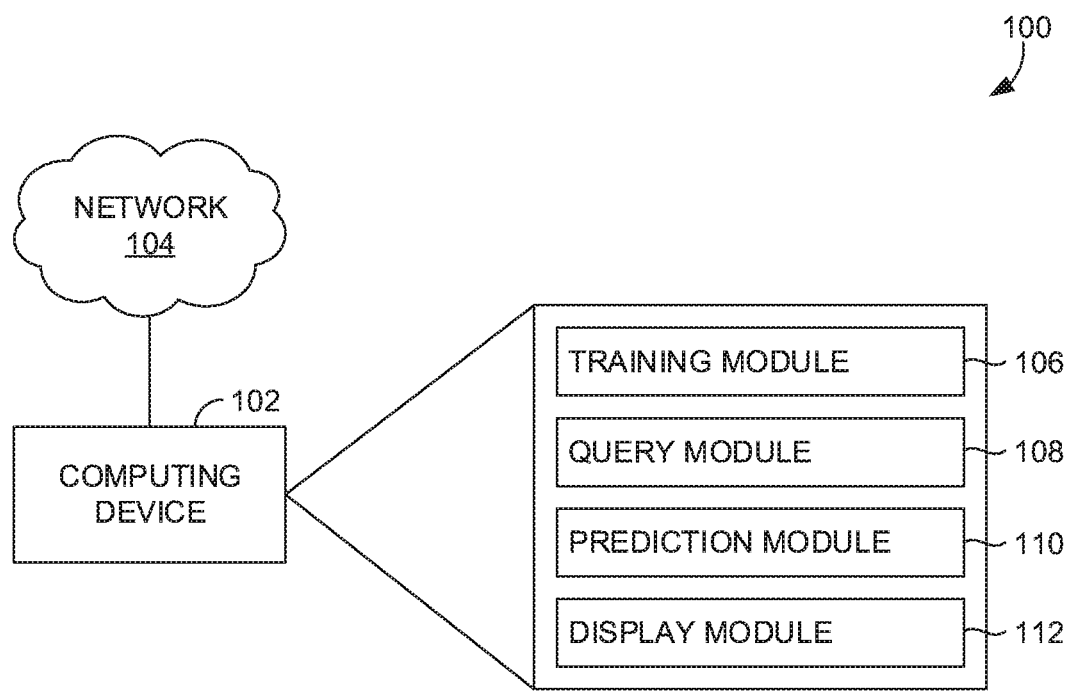
FIG. 1 illustrates an example environment having software and/or hardware components, in accordance with aspects.

The subject matter of the present invention is being described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Terms should not be interpreted as implying any particular order among or between various steps herein disclosed unless and except when the order of individual steps is explicitly described. As such, although the terms "step" and/or "block" can be used herein to connote different elements of system and/or methods, the terms should not be interpreted as implying any particular order and/or dependencies among or between various components and/or steps herein disclosed unless and except when the order of individual steps is explicitly described. The present disclosure will now be described more fully herein with reference to the accompanying drawings, which may not be drawn to scale and which are not to be construed as limiting. Indeed, the present invention can be embodied in many different forms and should not be construed as limited to the aspects set forth herein. Further, it will be apparent from this Detailed Description that the technological solutions disclosed herein are only a portion of those provided by the present invention. As such, the technological problems, solutions, advances, and improvements expressly referenced and explained herein should not be construed in a way that would limit the benefits, improvements, and/or practical application of the discussed aspects of the present invention.

Aspects herein provide methods, systems, and computer-readable media and methods for improved state identification and next state predictions in a neural network model trained using workflow and step data as input.

Previously, when a client or user ticket is electronically entered or logged, the user must describe their specific problem or issue in a pop-up messaging dialog. For example, the user might state that one or more aspects of a user interface or web-based application is not working or is causing an error. Then, for example, a support associate would attempt to recreate the problem within the user's specific domain within the user's workflow in order to troubleshoot the problem—a process requiring hours or even weeks to execute. In order to recreate the problem, the support associate would have to search for and identify the workflow that is specific to the user, in such an example. Without expert knowledge of a particular client's terminology and the inability to locate anything beyond an identical match, this search might be fruitless. The support associate would also have to determine the particular step within the user workflow where the problem is occurring. Only then can the support associate begin to attempt to recreate the problem and begin to troubleshoot the problem, in this example. Provided that a support associate may provide Information Technology (IT) services to hundreds or thousands of distinct users, each having their own customized workflow, the identification of a workflow and the step or state at issue is difficult, time consuming, and completely manual.

In aspects herein, methods, systems, and computer-readable media are provided that overcome the technological problems and technological limitations discussed above. Specifically, aspects herein train a neural network model using word embedding, generate multiple vector indices that correspond to workflows or steps, render the indices searchable through a graphical user interface, identify specific workflows and steps in response to searches using semantics to allow non-identical matching, and even predict succeeding steps for those steps identified via searches. In this manner, a specific workflow and even a specific step can be quickly located, without requiring knowledge of the particular client's identity and without requiring knowledge of the specific workflow of that client. Additionally, a specific workflow and even a specific step can be quickly located using minimal input such as a couple of words or a phrase, and further, without requiring exact word matching, as terminology varies greatly between users and clients. As used herein, the terms "step" and "state" may be used interchangeably herein to refer to a step in a workflow as well as the electronic state data that represents the step and its sequential placement within a workflow.

Even further, in aspects herein, when a particular step is identified as being the "current" state that is the subject a query, the directly subsequent or succeeding step from one or more possible workflows can be predicted by leveraging Markov chaining techniques within the semantic aspects of the neural network model. By applying a Markov chaining technique to predict succeeding states using a neural network model that was created and previously trained using word embedding, the aspects discussed herein can accurately predict whether one or more succeeding states and/or whether one or more different workflows are contextually and/or semantically similar. This particular combination produced a synergistic outcome, and thus the aspects herein provide a technological improvement over other methods or systems, which lacked the ability to recognize different steps and/or different workflows as being contextually and/or semantically similar.

Additionally, by training the neural network model using client or user interactions in addition to workflow and step data, the aspects herein overcome the technological limitations and constraints, specifically the lack of an adequate quantity of data (i.e., data scarcity) that wholly prevented anyone from creating a neural network model. Previously, a neural network model for workflows could not be created as there was insufficient data available to train. For example, workflow data alone might only account for approximately 30,000 documents, but this is too few documents to sufficiently create and train a model. In aspects herein, the neural network model is created and trained using 1.2 billion documents, by including client and user interactions as well as workflow and step data.

FIG. 1 illustrates an environment 100 with an example system having software and/or hardware components, in accordance with aspects. In aspects, the environment 100 includes a computing device 102 that is communicatively coupled to a network 104. In some aspects, the computing device 102 hosts one or more modules that form a system for improved state identification and prediction in computerized queries. Although shown in the singular, the computing device 102 may include a plurality of devices, such as computing devices, physical servers, virtual servers, local servers, and/or remote servers in the environment 100. Accordingly, the computing device 102 may be implemented in a distributed manner by connecting one or more computing devices using the network 104. The network 104 may be implemented as described in FIG. 16, in various aspects. The computing device 102 can include components such as a processing unit, internal system memory, and a suitable system bus for coupling to various components, including electronic storage, memory, and the like, such as a data store, a database, and/or a database cluster. Example components of the computing device 102 include a processing unit, internal system memory, and a suitable system bus for coupling various components, as further described herein with reference to FIG. 16. The computing device 102 includes or has access to a variety of non-transitory computer-readable media, as further described herein with reference to FIG. 16. Accordingly, the computing device 102 may be implemented as described in FIG. 16, in various aspects.

In some aspects, the computing device 102 includes one or more computer-executable instructions that can be read and executed via one or more hardware processors. The computing device 102 can include program modules, in such aspects. In some aspects, the computing device 102 includes one or more of a training module 106, a query module 108, a prediction module 110, and/or a display module 112. Using these modules, the computing device 102 can execute, perform, implement, and support the methods and systems further described herein.

In aspects, the training module 106 generates a model through word embedding. Then, the query module 108 searches the model using a query string to identify one or more semantic matches for the query string, in some aspects. Additionally, the query module 108 may, in response to searching the model, identify a plurality of results in the model, wherein the plurality of results correspond to semantic matches between the query string and one or more of a step or workflow in the model, in some aspects. In one aspect, the query module 108 determines probabilities for the plurality of results that represent semantic strength of the semantic matches. In some embodiments, the prediction module 110, in some aspects, predicts one or more additional results that are related to the plurality of results, wherein the one or more additional results correspond to semantic matches between the plurality of results and the one or more additional results. The display module 112 causes a ranked display of the plurality of results identified, the probabilities determined, and/or the one or more additional results predicted, in a graphical user interface (GUI), in various aspects.

Figure 2:
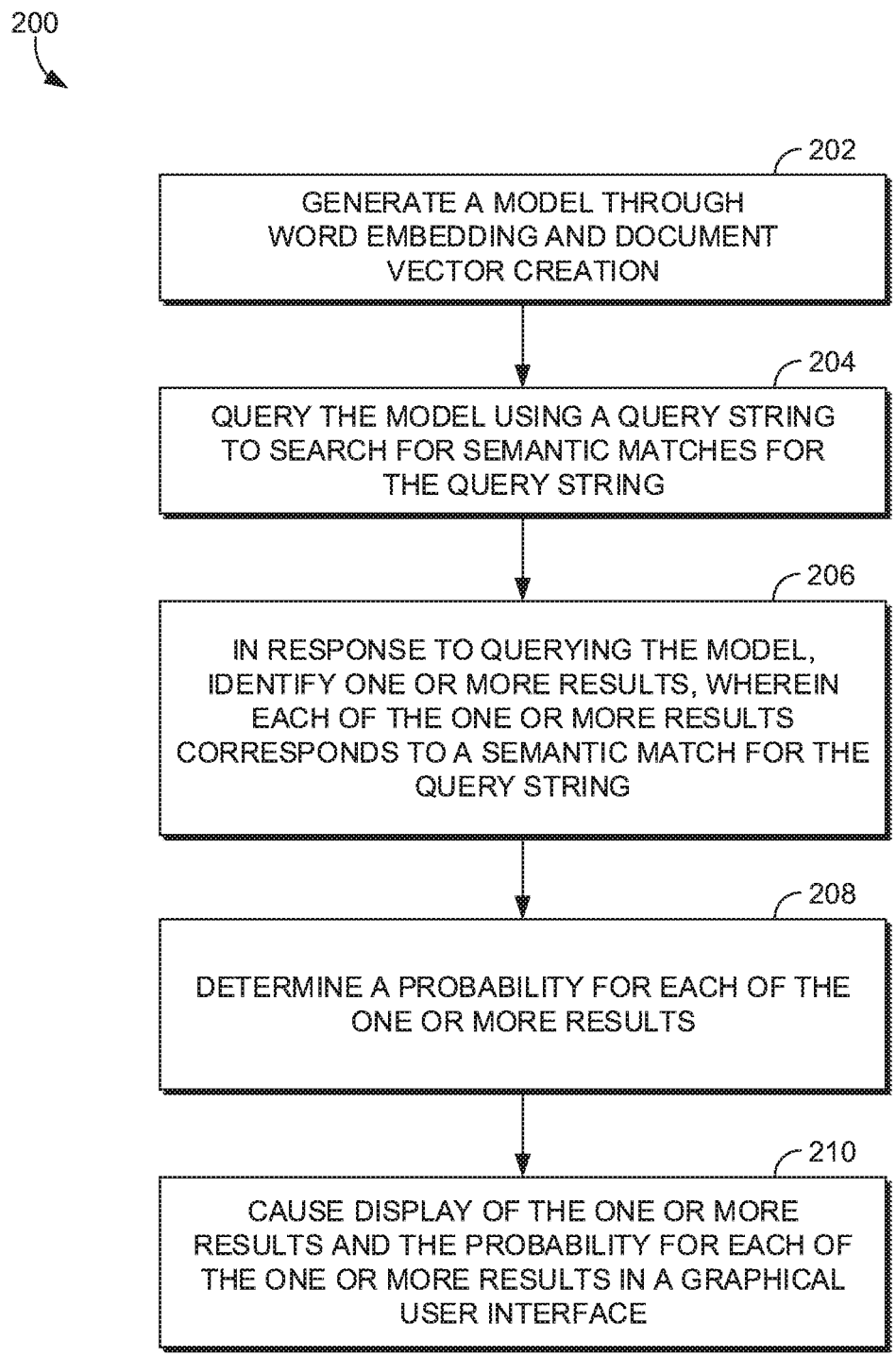
FIG. 2 depicts a method for improved state identification in computerized queries, in accordance with aspects.
Figure 3:
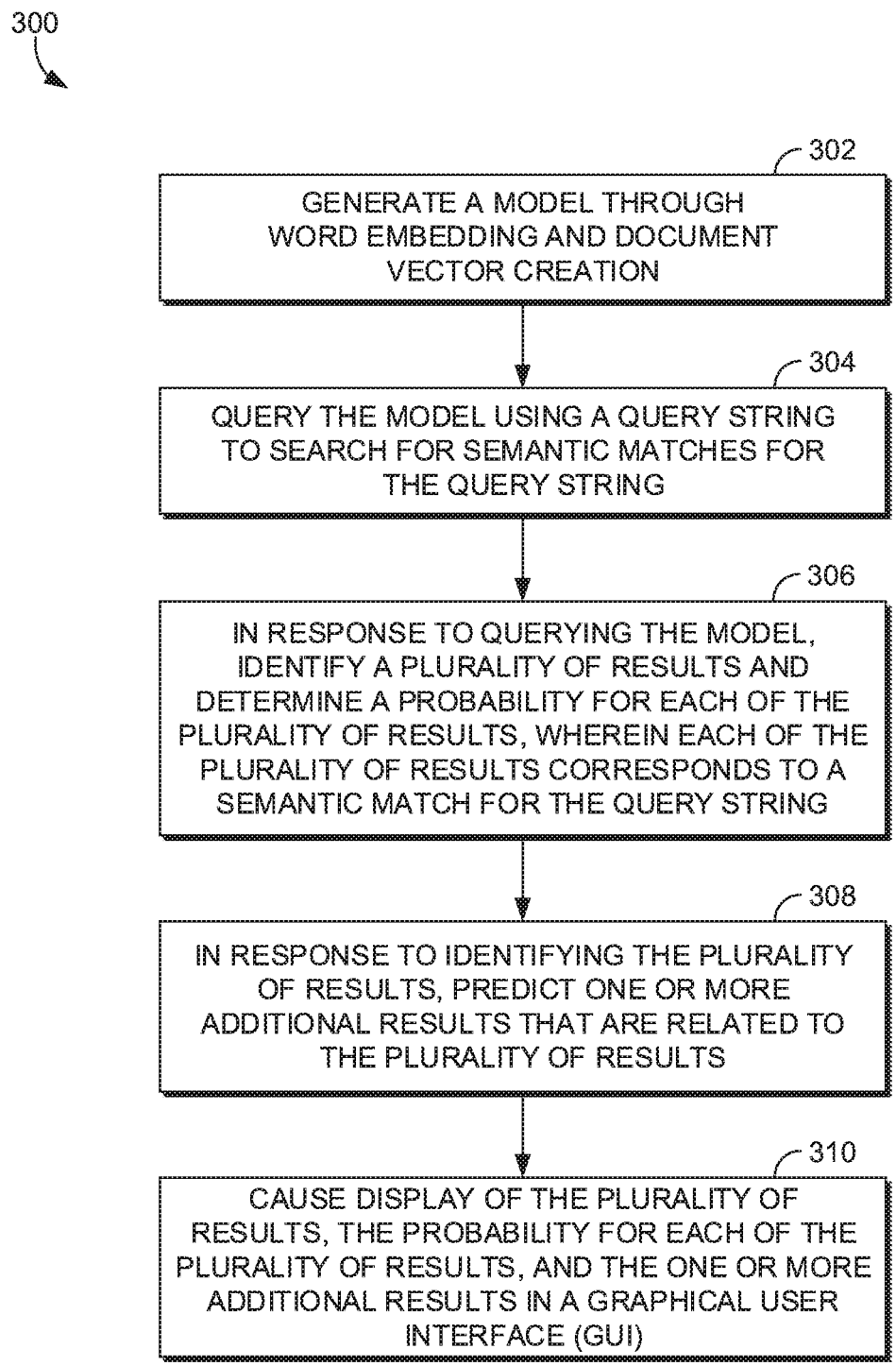
FIG. 3 depicts another method for improved state identification and prediction in computerized queries, in accordance with some aspects.

Turning now to FIGS. 2 and 3, methods are discussed that can be performed via one or more of the devices, components, and/or component interactions previously described in FIG. 1. It should be understood that the methods discussed herein can be implemented or performed via the execution of non-transitory computer-readable instructions and/or executable program code portions stored on computer readable media, using one or more processors. The computer-readable program code can correspond to the application, described above, wherein the application performs the methods, in some aspects. In aspects, the methods can be implemented and performed using a computerized application. As such, the methods can be computer-implemented methods, in some aspects, integrated with and executed to complement a computerized clinical workflow.

FIG. 2 depicts a method 200 for improved state identification in a neural network model trained using workflow and step data as input, in accordance with aspects. In some aspects, the method 200 can be performed, using one or more processors to execute computer-readable or machine instructions stored or embodied on a non-transitory computer-readable storage medium. As some aspects of the method 200 are previously described with regard to other methods herein, those aspects are only discussed briefly.

Figure 4:
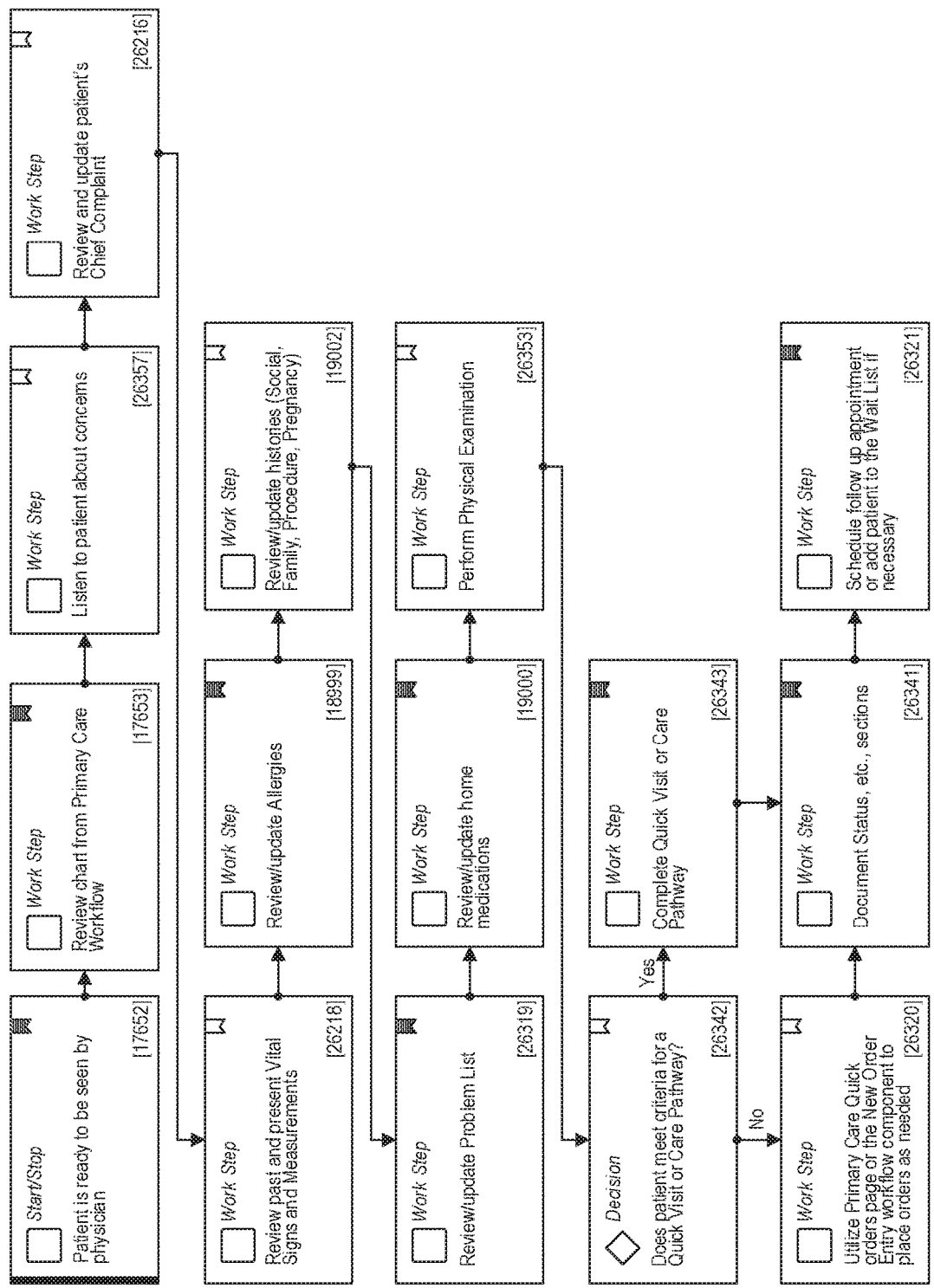
FIG. 4 depicts an example representation of raw data for a workflow and a plurality of steps, in accordance with aspects.

At block 202, a model is generated using word embedding. For example, workflow documents and data that includes a plurality of different or distinct user-specific workflows, each having multiple steps and/or complex branching, as well as user interaction documents and data, such as electronically logged client tickets detailing problems and concerns, online messaging and conversations between a client and support specialist, may be aggregated together. In this example, the documents may be raw data that is then converted into a plurality of structured data sets. For example, FIG. 4 depicts an example of a workflow having multiple steps defined in a specific sequence 400, where the workflow may act as input with the user interactions previously described, in accordance with aspects. FIG. 5 depicts an example of structured data 500 created from the data of FIG. 4, for example.

Figure 6:
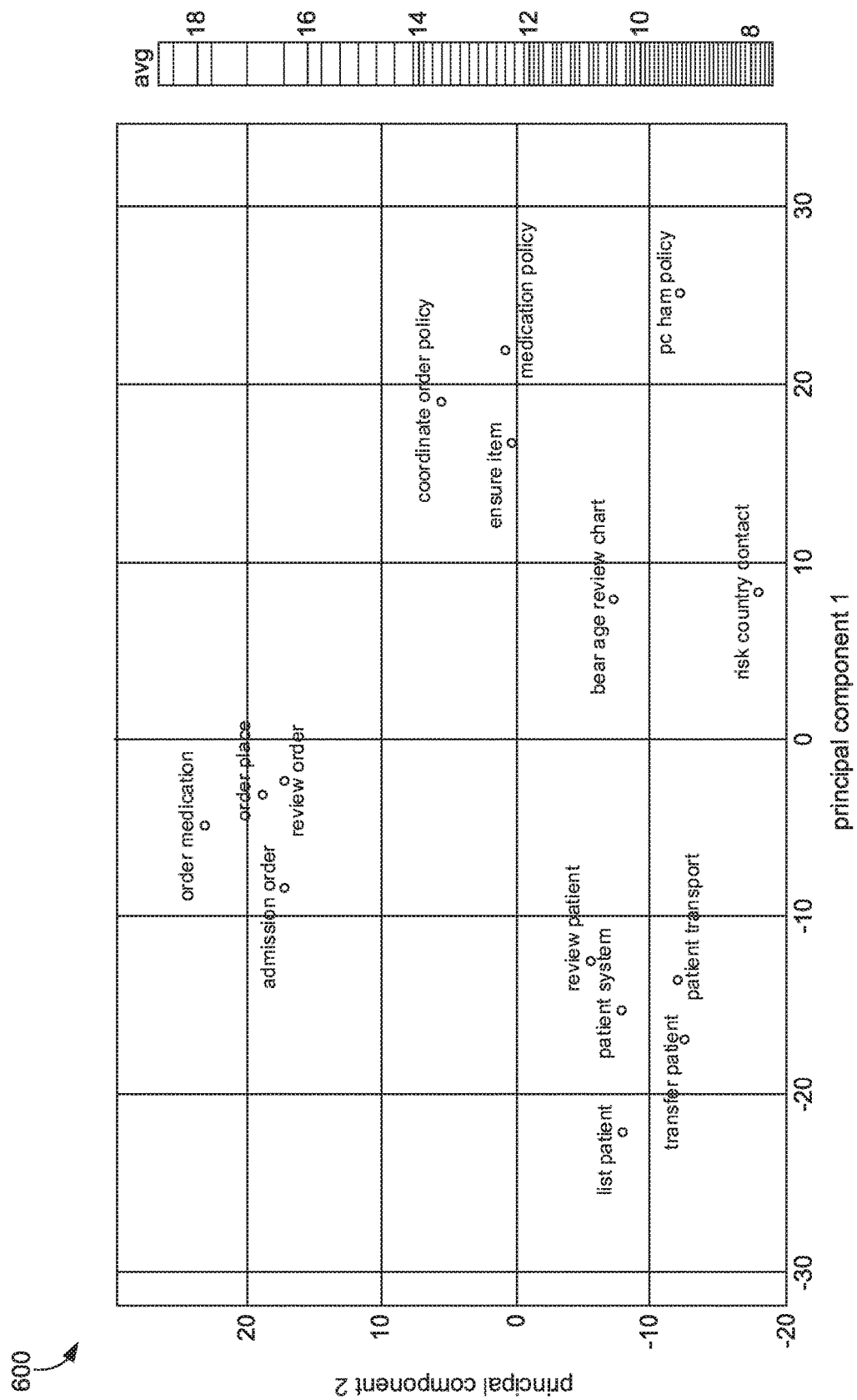
FIG. 6 depicts an example graphic representation of word embedding for training a neural network model, in accordance with aspects.
Figure 8:
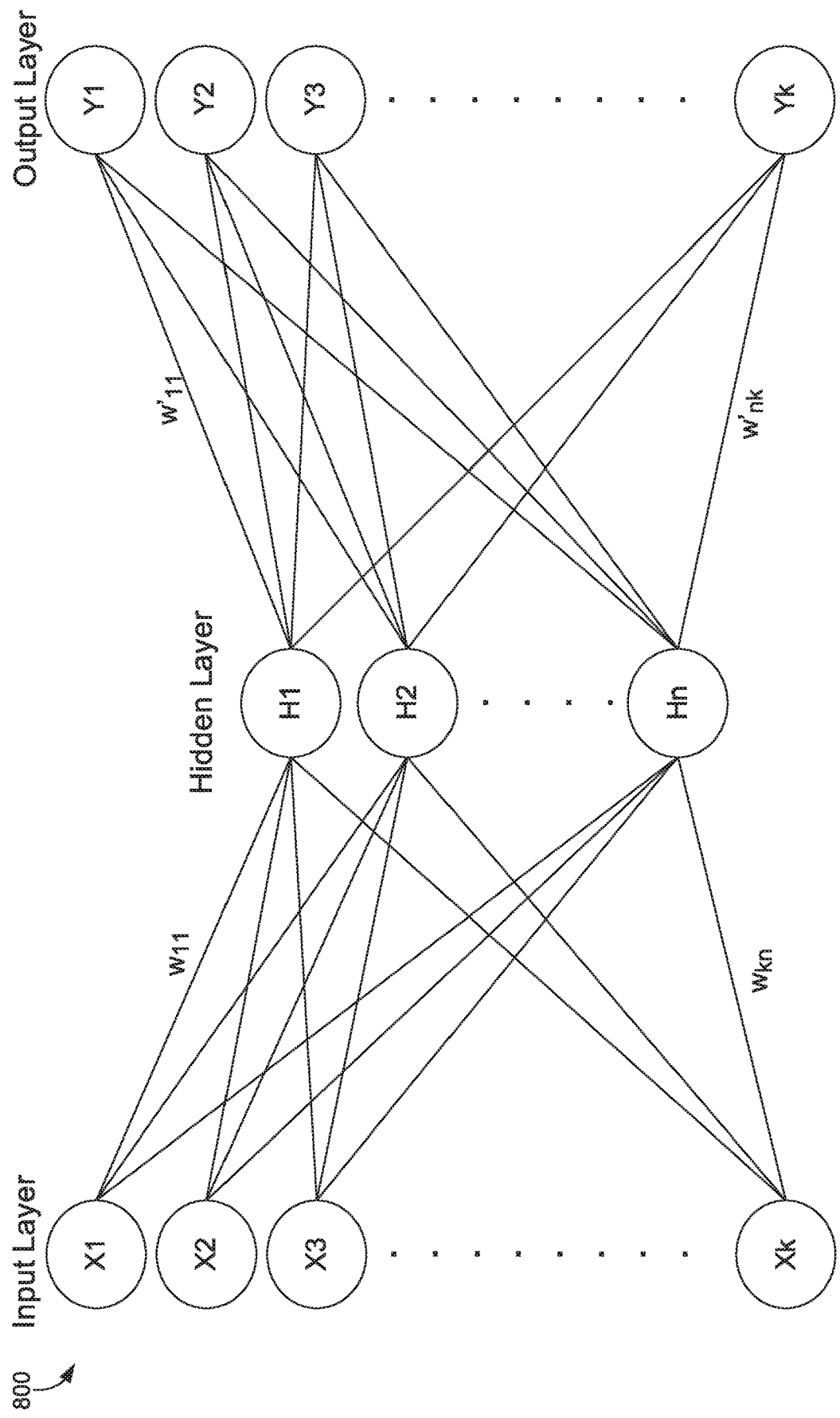
FIG. 8 depicts an simplified graphic representation of a neural network used to vectorize documents, strings, and text data, in accordance with aspects.

In some aspects, the model is generated by using the structured data sets to train a neural network model. For example, a plurality of multi-dimension document vectors can be created from a plurality of the workflow and interaction documents, and each of the plurality of multi-dimension document vectors may correspond to a different workflow. In another example, a plurality of multi-dimension document vectors are created from the workflow and interaction documents, and each of the plurality of multi-dimension document vectors corresponds to a distinct step in a workflow. In one example, a multi-dimension document vector is created for each document serving as input. An index of the plurality of multi-dimension document vectors may be created, in some aspects. In one aspect, one index is generated or created for vectors of documents that are specific to steps in a workflow, and another index is generated or created for vectors of documents that are specific to workflows. In one such aspect, one index may be searchable for steps and another index may be searchable to identify a particular workflow. FIG. 6 depicts an example graphic representation 600 of word embedding for training a neural network model, and FIG. 7 depicts an example representation of computer programming code 700 of a trained neural network model. It will be understood from this discussion and the figures herein that the conversion of raw input data into structured data, the creation of multi-dimensional vectors for the documents from the data, and the building of workflow- and step-specific indices refer to word embedding techniques that generate a model which accounts for and learns semantic meanings in documents, and thus, can relate documents to one another based on semantic meaning, for steps and workflows. FIG. 8 depicts a simplified graphic representation 800 of a neural network used to vectorize documents, strings, and text data.

At block 204, the model is queried using a string to identify semantic matches, in aspects. In one aspect, the query module 108 of the computing device 102 of FIG. 1 can query or search the model using a string to identify semantic matches, for example, in one or more indices of vectors from documents. For example, a string of alphanumeric characters forming words or phrases may be received as input via a graphical user interface, e.g., "specimen collection failing" is an example query string shown in FIG. 10. The model enables semantic matches based on the word embedding techniques used to create the model, as discussed hereinabove. As such, "specimen" may be used to locate and identify workflows that include an exact match for the query string and to identify workflows that include non-identical semantic matches for the query string, as further described below. Additionally or alternatively, "specimen" may be used to locate and identify specific steps in different workflows that include an exact match for the query string and to identify specific steps that include non-identical semantic matches for the query string, as further described below.

In one aspect, the model is queried using a string in order to identify semantic matches, and this further includes determining to query a first model using the string. The string comprises one or more words or phrases that may be input by a user and/or support associate through a graphical user interface. In such an aspect, it is determined that a first model is to be queried, either by default or by a user selection indicated that workflow identification is desired. The first model corresponds to a plurality of multi-dimension document vectors, and where each of the plurality of multi-dimension documents vectors corresponds to a distinct workflow. In order to perform the query, a multi-dimension query vector of the string can be generated for comparison to the multi-dimension document vectors in the first model that represent various workflows, in such an aspect. Accordingly, a user may conduct the query in order to identify a particular workflow as corresponding to, being associated with, and/or being responsive to the string.

In some aspects, querying the model using a string to identify semantic matches includes determining to query a first model using the string, either by default or by a user selection indicated that step identification is desired, for example. In an aspect, the first model corresponds to a plurality of multi-dimension document vectors, wherein each of the plurality of multi-dimension document vectors corresponds to a step. In order to perform the query, a multi-dimension query vector of the string may be generated for comparison to the multi-dimension document vectors in the first model that represent steps in various workflows. Accordingly, a user may search for a specific step across multiple different workflows.

Continuing, at block 206, in response to querying the model, one or more results are identified that correspond to the semantic matches identified. In one aspect, the query module 108 of the computing device 102 of FIG. 1 identifies one or more results that correspond to the semantic matches identified. For example, one or more results are identified based the cosine similarity score determined between the query vector and the plurality of multi-dimension document vectors in an index of the first model. In one such example, one or more of the plurality of multi-dimension document vectors from the index may be selected based on the cosine similarity with the query vector, wherein the one or more selected multi-dimension document vectors are thus determined to be served back and returned as one or more results. The one or more results may be identified, for example, wherein the cosine similarity score ranges from +1 to ~1, where +1 indicates increasing similarity relative to the query vector (i.e., generated from the query string), and wherein −1 indicates decreased similarity relative to the query vector. As such, the cosine similarity score is calculated to determine how similar the query string is relative to the documents represented by the vectors in the model, in various aspects. It will be understood that the use of cosine similarity is just one method that may be employed to assess the similarity of vectors relative to one another, and that other techniques are contemplated and considered to be within the scope of this disclosure, for use alone or in combination with cosine similarity. As such, the utilization of cosine similarity here is not to be construed as limiting.

Figure 9:
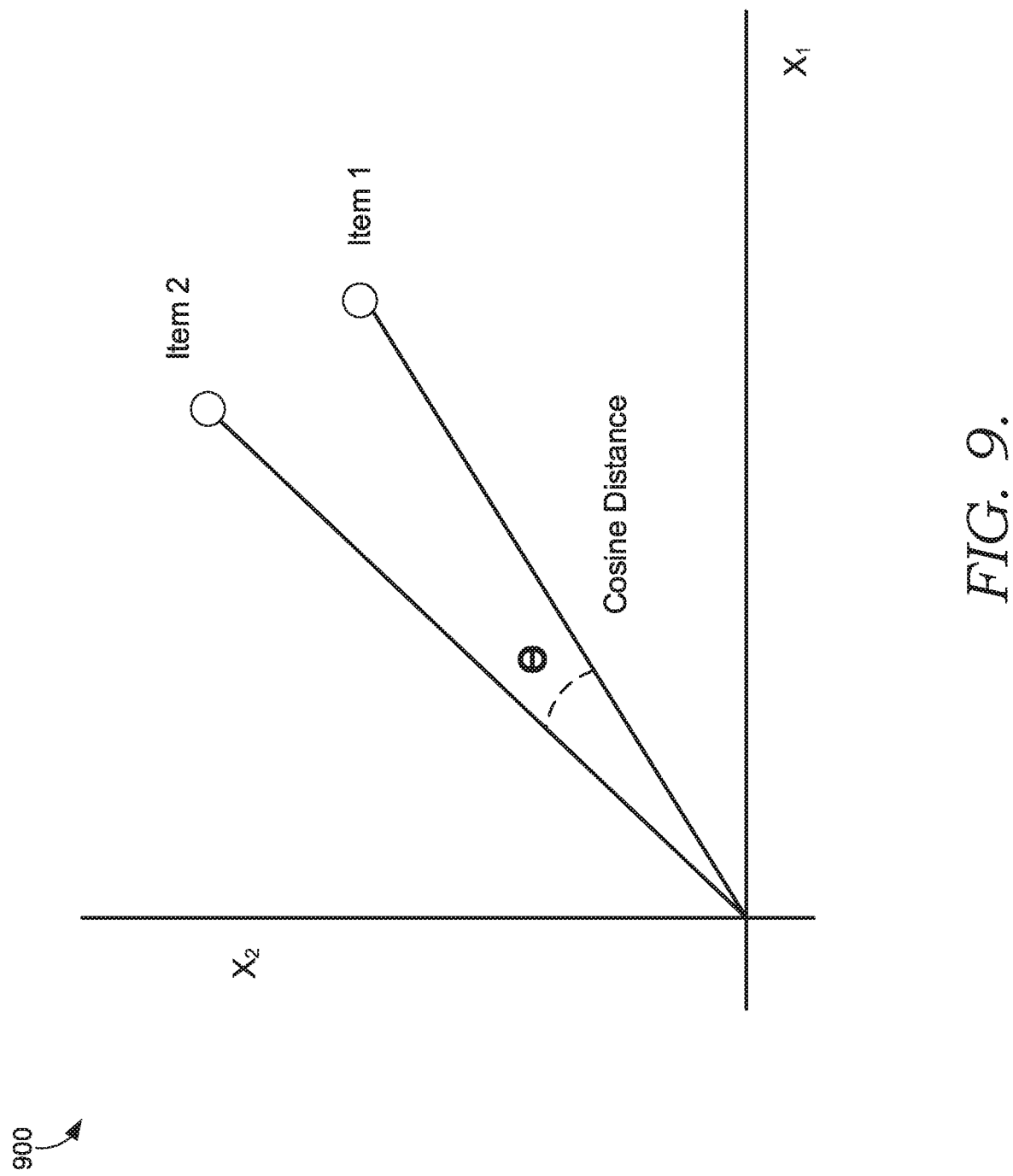
FIG. 9 depicts an simplified graphic representation of cosine similarity determinations between a document vector and a query string vector, in accordance with aspects.

At block 208, probabilities for the one or more results are determined that represent semantic strength of the semantic matches. In one aspect, the query module 108 of the computing device 102 of FIG. 1 can determine one or more probabilities for the one or more results, where the probabilities represent and/or quantify the semantic strength of the semantic matches between the results and the query string. The one or more probabilities correspond to the likelihood that the result is a semantic match to the string query, and as such, the one or more probabilities may be quantified as cosine similarity scores, in one aspect. As such, the probabilities may be determined by using the separate cosine similarity scores that are/were determined for the query vector and each of the plurality of multi-dimension document vectors in an index of the first model, in some aspects. Thus, for the one or more of the plurality of multi-dimension document vectors selected from the index based on the cosine similarity with the query vector, which might be selected for meeting or exceeding a cosine similarity score of zero or greater (e.g., a cosine similarity score in the range of 0 to +1), the cosine similarities may stand in for the probabilities determined. FIG. 9 depicts a simplified graphic representation 900 of cosine similarity determinations between a document vector and a query string vector, in accordance with aspects.

At block 210, the method 200 causes a ranked display of the one or more results and the probabilities in a graphical user interface. In one aspect, the display module 112 of the computing device 102 of FIG. 1 can cause the ranked display of the one or more results and the probabilities in a graphical user interface. For example, FIG. 10 depicts an example of a graphical user interface 1000 for presenting one or more of the identified results obtained by querying the trained neural network model. In one example, a search term of "specimen" may return steps or workflows with non-identical, semantic matches, such as "sample."

In a further embodiment based on the method 200, a neural network model is trained to create a plurality of 500-dimension document vectors for steps/states, wherein each of the plurality of the 500-dimension document vectors corresponds to distinct steps. Further, a first index of the plurality of the 500-dimension document vectors that corresponds to distinct work steps may be created. Additionally, the neural network model may be trained to create a plurality of 500-dimension document vectors for workflows, wherein each of the plurality of the 500-dimension document vectors corresponds to distinct workflows (e.g., identifies the workflow and not individual steps), in one aspect. In such aspects, a second index of the plurality of the 500-dimension document vectors that corresponds to distinct workflows can be created. Then, in order to perform a query, a 500-dimension query vector of the string of the query is generated using the same vectorization techniques used to train the neural network model. By determining the cosine similarity score between the 500-dimension query vector and the plurality of 500-dimension document vectors in the first index or the second index, semantic matches can be identified and selected. For example, one or more of the plurality of 500-dimension document vectors may be selected from the first index or the second index based on the vector(s)' cosine similarity with the query vector, wherein the one or more selected 500-dimension document vectors are the one or more results. The selected results may have a cosine similarity that meets a minimum threshold (e.g., 0 or greater), or the selected results may be the ten results having the highest cosine similarity, independent of any particular threshold.

Turning now to FIG. 3, another method 300 for improved state identification and prediction in computerized queries is shown, in accordance with some aspects. In some aspects, the method 300 can be performed, using one or more processors to execute computer-readable or machine instructions stored or embodied on a non-transitory computer-readable storage medium. As some aspects of the method 300 are previously described with regard to other methods herein, those aspects are only discussed briefly.

At block 302, a model is generated through word embedding. In one aspect, the training module 106 of the computing device 102 of FIG. 1 can generate a model through word embedding. In some aspects, data from a plurality of distinct workflows is electronically aggregated, and the plurality of distinct workflows corresponds to a plurality of entities. In one such aspect, a probability table is created using the aggregated data. The probability table includes a plurality of probabilities for a plurality of vectors and the plurality of vectors correspond to preceding steps, current steps, and succeeding steps from the plurality of distinct workflows. Each of the plurality of probabilities corresponds to a calculated likelihood of a preceding step and a succeeding step relative to a current step, for each step within each of the plurality of distinct workflows, in various embodiments. In one example, the probability table may store probabilities for Markov Chaining determinations. For example, the probability table may store values for the likelihood that Step A precedes Step B as 80% in Workflow AAA, and the value for the likelihood that Step A precedes Step C as 20% in Workflow AAA. In one example, the probability table may store values for the likelihood that Step A precedes Step C as 65% in Workflow AAA, and the value for the likelihood that Step A precedes Step C as 54% in Workflow BBB. The probabilities in the table may be based on and/or calculated based on the workflow and user interaction action data used in generating the model, in some aspects.

Continuing, at block 304, the model is searched using a query string to identify one or more semantic matches for the query string. In one aspect, the query module 108 of the computing device 102 of FIG. 1 can search the model using a query string in order to identify one or more semantic matches for at least a portion of the query string. In order to perform the search, a query vector of the query string may be generated, in an aspect. The probability table in the model may then be queried to identify a first vector that is most similar to the query vector, in some aspects. The first vector may correspond to a current step or a preceding step in one or more workflows. In some aspects, based on the first vector that is identified via querying the probability table of the model, a second query may be performed. For example, the second query may search the probability table to identify a second vector that has the highest probability of corresponding to an immediately succeeding step relative to the preceding step or the current step of the first vector. As such, the query string may be used to identify multiple vectors that correspond to a possible current step that have a high likelihood of corresponding to the query string, as well as possible preceding steps and possible succeeding steps relative to the current step.

At block 306, in response to searching the model, a plurality of results are identified in the model, where the plurality of results correspond to semantic matches between the query string and one or more of a step or workflow in the model. In one aspect, the query module 108 of the computing device 102 of FIG. 1 can identify a plurality of results in the model, in response to searching the model, where the results correspond to semantic matches of the query string and one or more steps and/or one or more workflows in the model.

At block 308, probabilities for the plurality of results are determined that represent semantic strength of the semantic matches. In one aspect, the query module 108 of the computing device 102 of FIG. 1 can determine probabilities for the plurality of results that represent the semantic strength of the semantic matches. For example, it may be determined whether one or more of the vectors in the model at least meet a threshold likelihood (e.g., a minimum value) of semantically matching the query vector. The strength of the semantic match may be measured as a cosine similarity from a vector-to-vector comparison.

Figure 11:
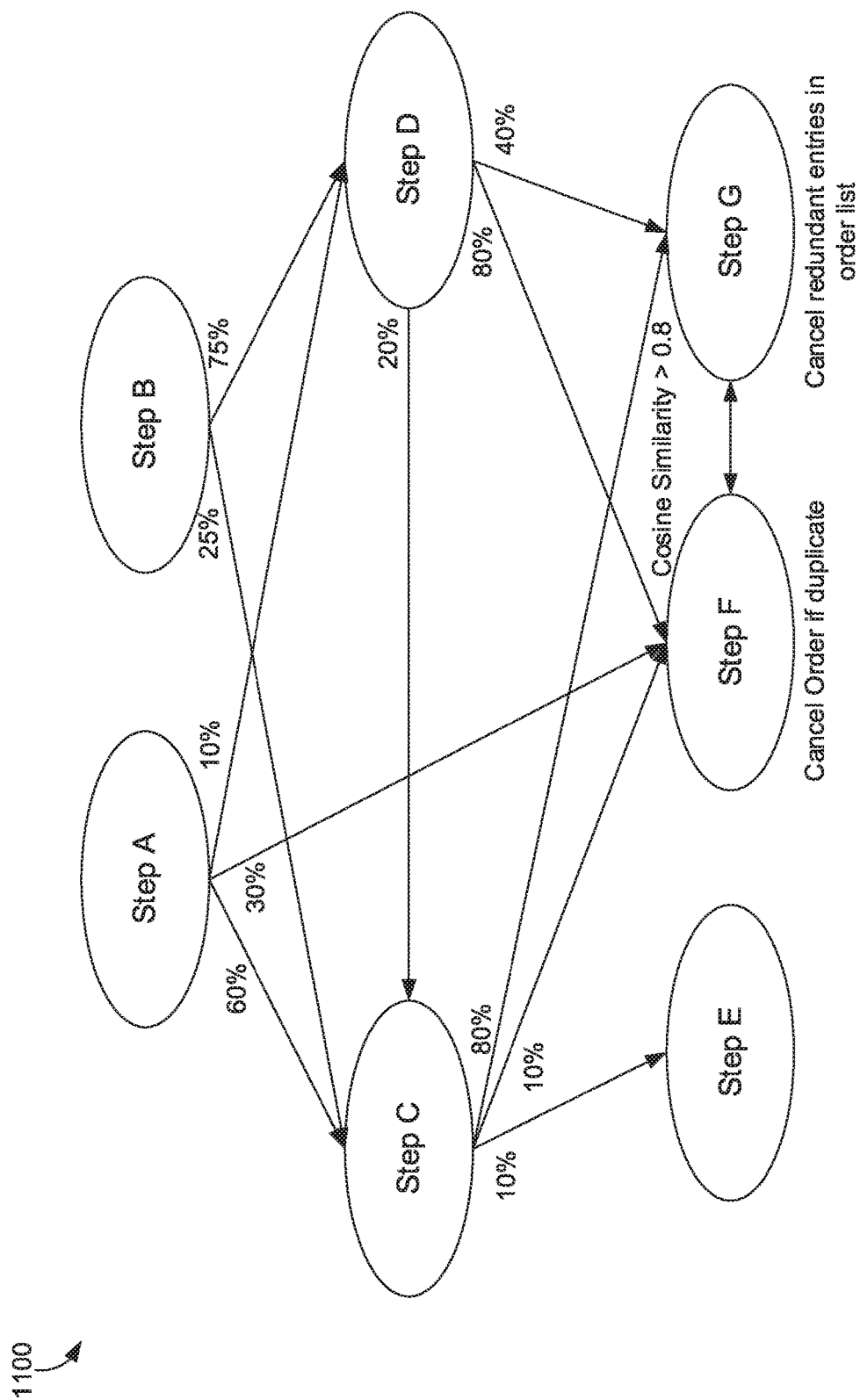
FIG. 11 depicts an simplified graphic representation of Markov Chaining predictions using the trained neural network model, in accordance with some aspects.

At block 310, one or more additional results are predicted that are related to the plurality of results, where the one or more additional results correspond to semantic matches between the plurality of results and the one or more additional results. In one aspect, the prediction module 110 of the computing device 102 of FIG. 1 can predict one or more additional results that are related to the plurality of results initially identified using the query. For example, the one or more additional results may be determined as predicted to correspond to possible preceding steps and/or possible succeeding steps relative to one or more current steps, where the current step(s) correspond to the one or more results identified initially. The probability table and Markov chaining techniques may be used to identify which of the vectors in the model have at least a threshold likelihood of being a directly preceding step and/or a directly succeeding step relative to a current step, wherein the current step corresponds to the one or more results (i.e., vectors) initially identified using cosine similarity relative to the query vector. FIG. 11 depicts a simplified graphic representation 1100 of Markov Chaining predictions using the trained neural network model, in accordance with some aspects.

Accordingly, the initial query may be used to identify a current step/state that corresponds to one of the plurality of results based on semantic matching. The results may correspond to a current state in a workflow, based on the query. Then, for each of the results, Markov chaining may be used to predict, based on the current state, one or more directly preceding and/or directly succeeding states in one or more different workflows. In one example, Markov chaining is used to identify, for each one of the plurality of results, a current state (based on the result), a prior or preceding state, and a succeeding state. The succeeding state may be predicted based on the current step alone, or based on the current step and the predicted preceding step together.

Figure 12:
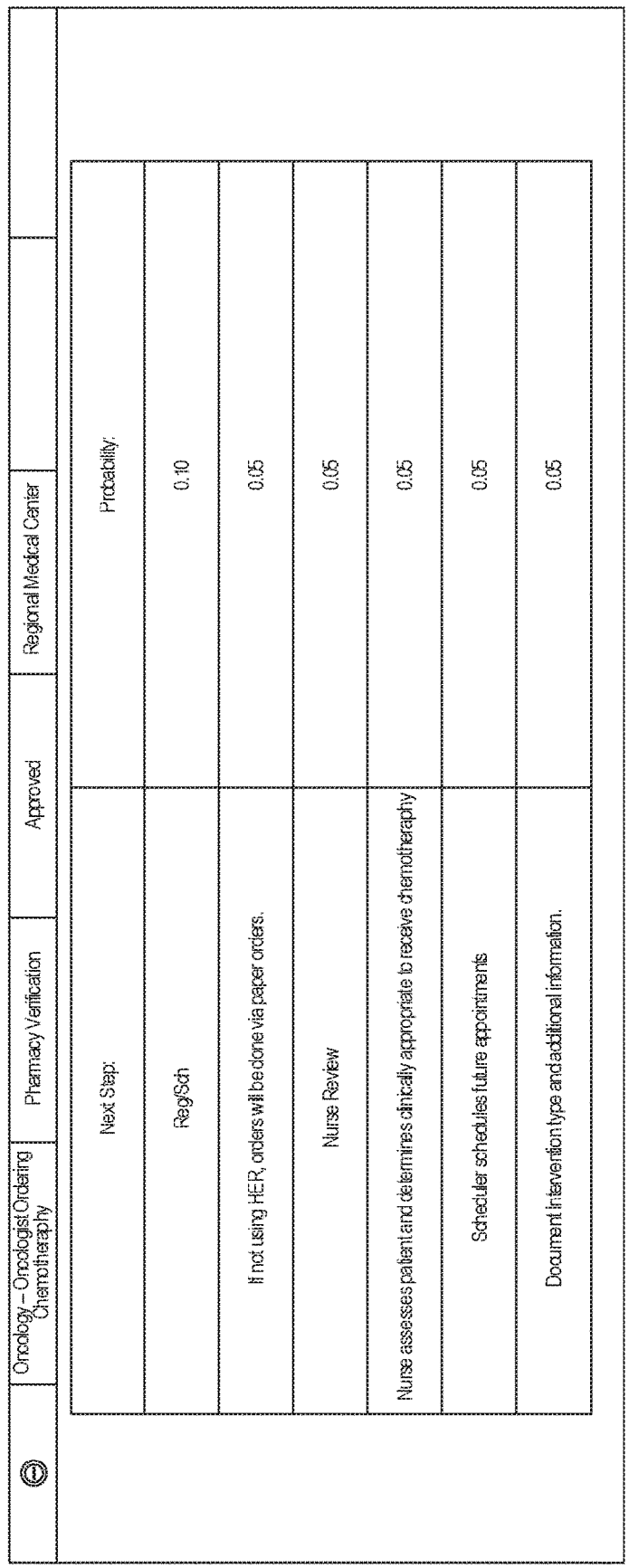
FIG. 12 depicts an example of a graphical user interface for presenting predictions based on the trained neural network model, in accordance with some aspects.

At block 312, a ranked display of the plurality of results identified, the probabilities determined, and the one or more additional results predicted, are presented in a graphical user interface (GUI). In one aspect, the display module 112 of the computing device 102 of FIG. 1 can cause the ranked display of the plurality of results identified, the probabilities determined, and the one or more additional results predicted. FIG. 12 depicts an example of a graphical user interface 1200 for presenting predictions based on the trained neural network model, in accordance with some aspects. The results, which may identify current states in one or more workflows, may be displayed and ranked from greatest cosine similarity with the query vector, in a descending or ascending sequence or order, in some aspects. The predicted additional results, which may identify predicted succeeding steps in one or more workflows, may be displayed and ranked from greatest probability of relatedness to the current state, and shown in a descending or ascending sequence or order, in various aspects.

Figure 13:
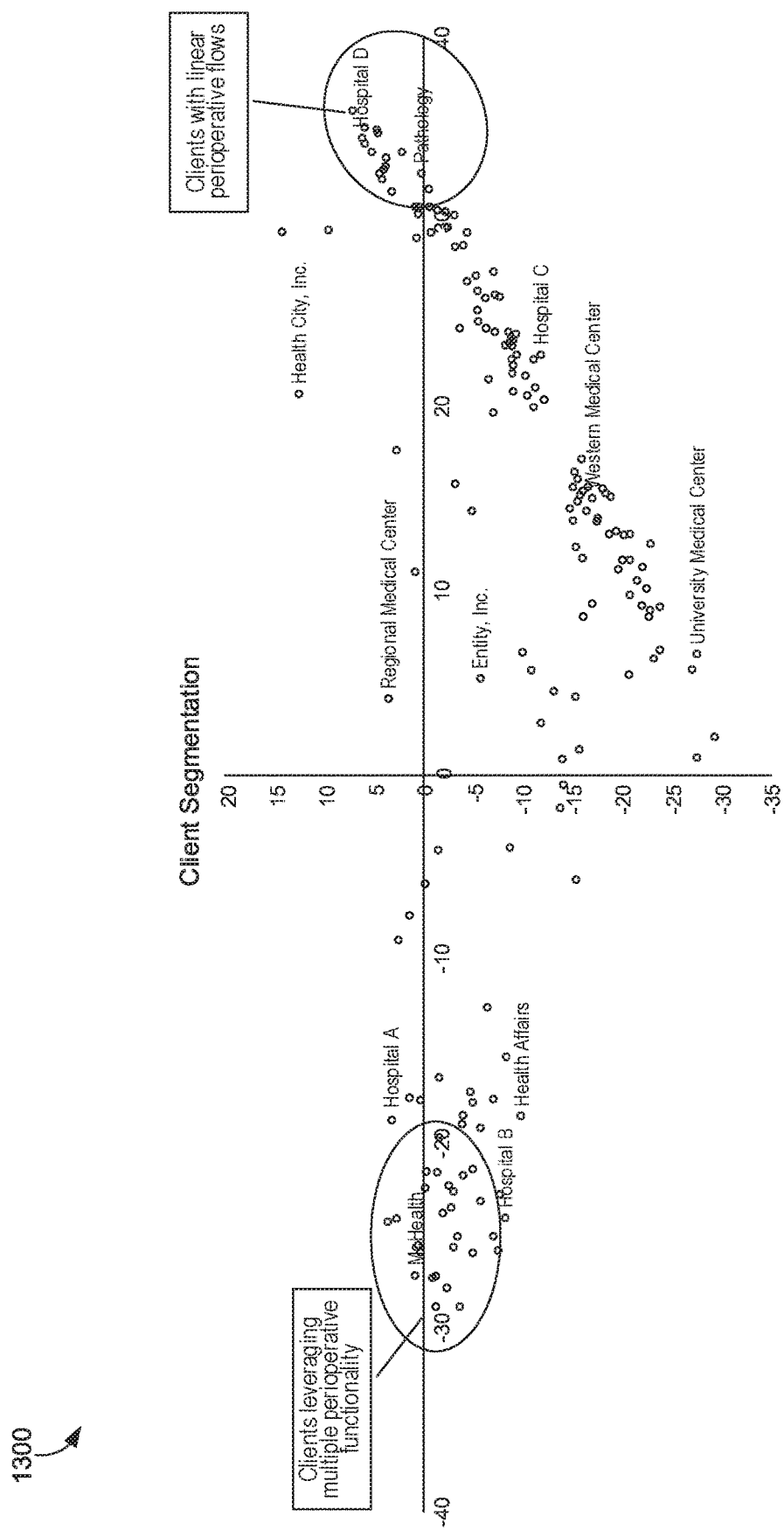
FIG. 13 depicts a simplified graphic representation of distinct entities grouped by similarity of workflow and/or steps, in accordance with some aspects.
Figure 15:
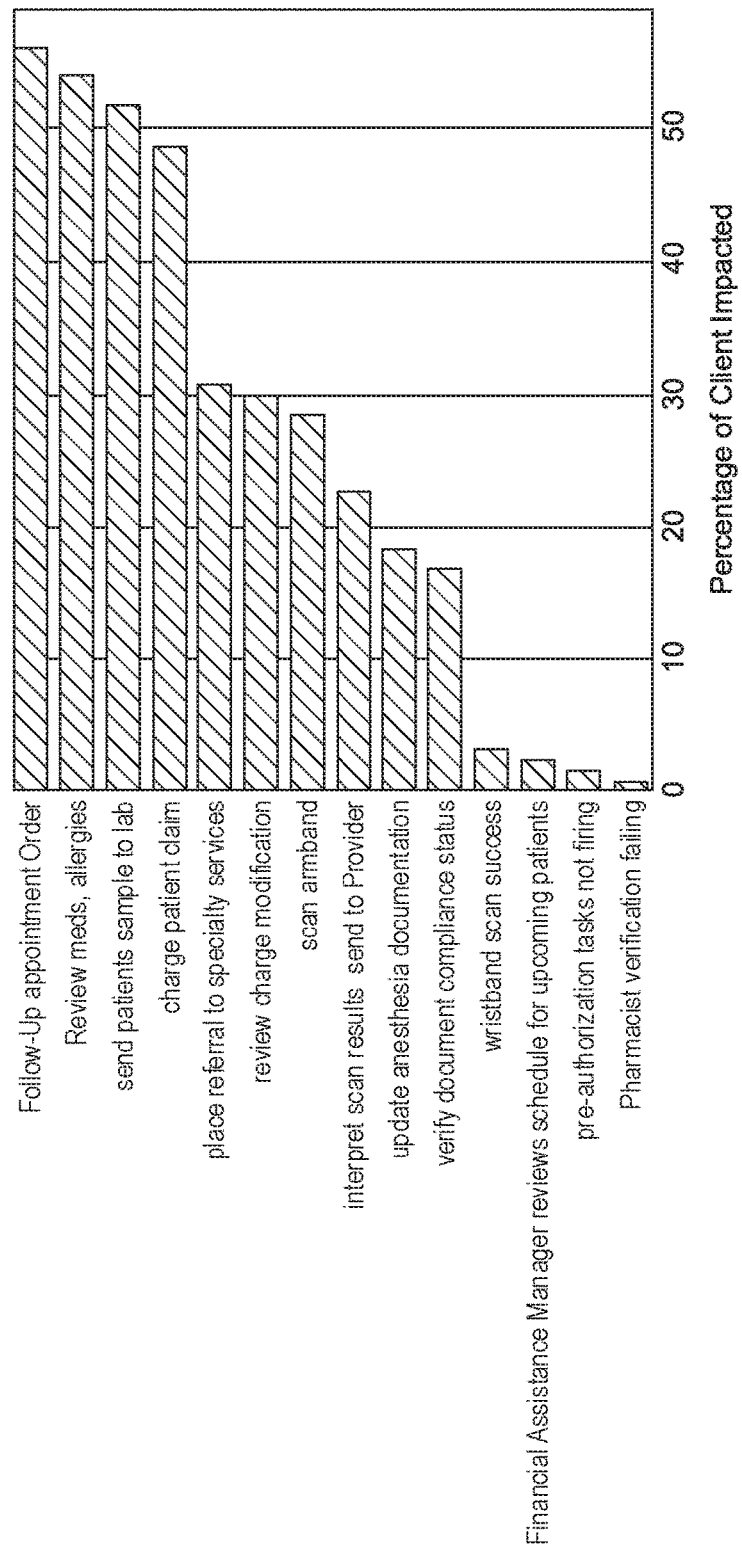
FIG. 15 depicts an example graphic representation of predicted impacts across distinct entities based on workflow and/or step similarities, in accordance with some aspects.

In addition to the aspects above, some aspects can further identify one or more workflows that are similar or related to one or more of the results, where the results correspond to a workflow. Additionally, based on the similarity or relatedness of the workflows, aspects herein may identify and group a plurality of users (e.g., clients or entities). For example, segmentation may be used to create cohorts of the clients or users associated with the plurality of workflows that acted as input to create and train the model. FIG. 13 depicts a simplified graphic representation 1300 of distinct entities grouped by similarity of workflow and/or steps, and FIG. 14 depicts an example of a table 1400 showing workflow and/or step similarity determinations across distinct entities, in accordance with some aspects. Based on these groupings, the results of queries and the predicted additional results of one user may be utilized for or recommended to other users in the same grouping. Further still, the impacts of specific steps/states that are present in different workflows for different clients may also be assessed. FIG. 15 depicts an example graphic representation of predicted impacts across distinct entities based on workflow and/or step similarities, in accordance with some aspects. As such, aspects create visibility that identifies which specific clients or users are using particular steps, and/or are using the same steps as the client or user's specific workflow, which further allows for improved troubleshooting and prioritization of development efforts based on the workflow used by an increasing percentage of clients for the same steps in different workflows.

Figure 16:
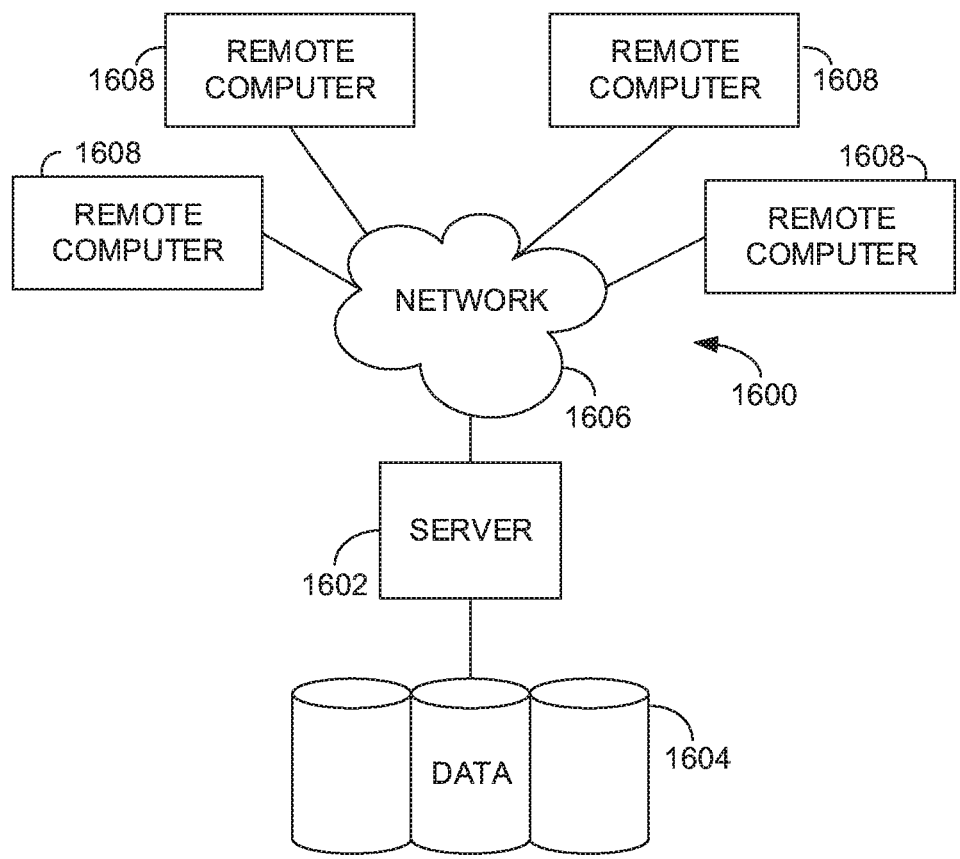
FIG. 16 depicts an example environment in accordance with some aspects.

Turning to FIG. 16, a computing environment 1600 that is suitable for use in implementing aspects of the present invention is depicted. The computing environment 1600 is merely an example of one suitable computing environment and is not intended to suggest any limitation as to the scope of use or functionality of the invention. Neither should the computing environment 1600 be interpreted as having any dependency or requirement relating to any single component or combination of components illustrated therein. Generally, in aspects, the computing environment 1600 is a medical-information computing-system environment. However, this is just one example and the computing environment 1600 can be operational with other types, other kinds, or other-purpose computing system environments or configurations. Examples of computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

In aspects, the computing environment 1600 can be described in the general context of computer instructions, such as program modules, applications, and/or extensions, being read and executed by a computing device. Examples of computer instructions can include routines, programs, objects, components, and/or data structures that perform particular tasks or implement particular abstract data types. The aspects discussed herein can be practiced in centralized and/or distributed computing environments, i.e., where computer tasks are performed utilizing remote processing devices that are linked through a communications network, whether hardwired, wireless, or a combination thereof. In a distributed configuration, computer instructions might be stored or located in association with one or more local and/or remote computer storage media (e.g., memory storage devices). Accordingly, different portions of computer instructions for implementing the computer tool in the computing environment 1600 may be executed and run on different devices, whether local, remote, stationary, and/or mobile.

With continued reference to FIG. 16, the computing environment 1600 comprises a computing device 1602, shown in the example form of a server. Although illustrated as one component in FIG. 16, the present invention can utilize a plurality of local servers and/or remote servers in the computing environment 1600. The computing device 1602 can include components such as a processing unit, internal system memory, and a suitable system bus for coupling to various components, including electronic storage, memory, and the like, such as a data store, a database, and/or a database cluster. Example components of the computing device 1602 include a processing unit, internal system memory, and a suitable system bus for coupling various components, including a data store 1604, with the computing device 1602. An example system bus might be any of several types of bus structures, including a memory bus or memory controller, a peripheral bus, and a local bus, using any of a variety of bus architectures. Examples of bus architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The computing device 1602 includes or has access to a variety of non-transitory computer-readable media. Computer-readable media can be any available media that is locally and/or remotely accessible by the computing device 1602, and includes volatile, nonvolatile, removable, and non-removable media. By way of example, and not limitation, computer-readable media can comprise computer storage media and communication media. Computer storage media includes volatile, nonvolatile, removable, and non-removable media, as implemented in any method or technology for storage of information, such as computer-readable instructions, data structures, program modules, or other data.

The computing device 1602 can include or can have access to computer-readable media. Computer-readable media can be any available media that can be accessed by computing device 1602, and includes volatile and nonvolatile media, as well as removable and non-removable media. By way of example, and not limitation, computer-readable media can include computer storage media and communication media.

Computer storage media can include, without limitation, volatile and nonvolatile media, as well as removable and non-removable media, implemented in any method or technology for storage of information, such as computer-readable instructions, data structures, program modules, or other data. In this regard, computer storage media can include, but is not limited to, Random Access Memory (RAM), Read-Only Memory (ROM), Electrically Erasable Programmable Read-Only Memory (EEPROM), flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which can be accessed by the computing device 1602. Computer storage media does not comprise signals per se.

Communication media typically embodies computer-readable instructions, data structures, program modules, or other data in a modulated data signal, such as a carrier wave or other transport mechanism, and can include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, radio frequency (RF), infrared, and other wireless media. Combinations of any of the above also can be included within the scope of computer-readable media.

The computing device 1602 might operate in a network 1606 using logical connections to one or more remote computers 1608. In some aspects, the one or more remote computers 1608 can be located at a variety of locations, such as medical facilities, research environments, and/or clinical laboratories (e.g., molecular diagnostic laboratories), as well as hospitals, other inpatient settings (e.g., surgical centers), veterinary environments, ambulatory settings, medical billing offices, financial offices, hospital administration settings, home healthcare environments, and/or clinicians' offices). As used herein, "clinicians," "medical professionals," or "healthcare providers" can include: physicians; specialists such as surgeons, radiologists, cardiologists, and oncologists; emergency medical technicians; physicians' assistants; nurse practitioners; health coaches; nurses; nurses' aides; pharmacists; dieticians; microbiologists; laboratory experts; laboratory technologists; genetic counselors; researchers; veterinarians; students; and the like.

In aspects, the computing device 1602 uses logical connections to communicate with one or more remote computers 1608 within the computing environment 1600. In aspects where the network 1606 includes a wireless network, the computing device 1602 can employ a modem to establish communications with the Internet, the computing device 1602 can connect to the Internet using Wi-Fi or wireless access points, or the server can use a wireless network adapter to access the Internet. The computing device 1602 engages in two-way communication with any or all of the components and devices illustrated in FIG. 16, using the network 1606. Accordingly, the computing device 1602 can send data to and receive data from the remote computers 1608 over the network 1606.

The network 1606 is a computer network that can include local area networks (LANs) and/or wide area networks (WANs), in some aspects. The network 1606 can include wireless and/or physical (e.g., hardwired) connections. Examples of networks include a telecommunications network of a service provider or carrier, Wide Area Network (WAN), a Local Area Network (LAN), a Wireless Local Area Network (WLAN), a cellular telecommunications network, a Wi-Fi network, a short range wireless network, a Wireless Metropolitan Area Network (WMAN), a Bluetooth® capable network, a fiber optic network, or a combination thereof. When the network 1606 includes a WAN-type configuration, the computing device 1602 might comprise a modem or other means for establishing communications over the WAN, such as the Internet, in such aspects. As such, the network 1606, can provide the components and devices access to the Internet and web-based applications.

The network 1606 can include an entity-wide network, campus-wide network, an office-wide network, an enterprise-wide networks, and the Internet. In the network 1606, applications, extensions, program modules or portions thereof might be stored in association with the computing device 1602, the data store 1604, and any of the one or more remote computers 1608. For example, various application programs can reside on the memory associated with any one or more of the remote computers 1608. In the computing environment 1600, which is illustrated as being a distributed configuration of the network 1606, the components and devices can communicate with one another and can be linked to each other using a network 1606. It will be appreciated by those of ordinary skill in the art that the network connections shown are exemplary and other means of establishing a communications link between the computers (e.g., computing device 1602 and remote computers 1608) might be utilized.

In operation, an organization might enter commands and information into the computing device 1602 or convey the commands and information, for example, directly in peer-to-peer or near-field communication, or through the network 1606 using telecommunications or Wi-Fi, to the computing device 1602 via one or more of the remote computers 1608 through input devices, such as a keyboard, a pointing device (e.g., a mouse), a trackball, as stylus, or a touch pad. Other input devices comprise microphones, satellite dishes, scanners, or the like. Commands and information might also be sent directly from a remote healthcare device to the computing device 1602. In addition to a screen, monitor, or touchscreen component, the computing device 1602 and/or remote computers 1608 might comprise other peripheral output devices, such as speakers and printers.

The computing environment 1600 includes one or more remote computers 1608, which may be accessed by the computing device 1602 over the network 1606 or directly using peer-to-peer connections or mesh networking, in various aspects. The remote computers 1608 might be servers, routers, network personal computers, peer devices, network nodes, computing devices, personal digital assistants, personal mobile devices, medical devices, patient monitoring equipment, or the like, and might comprise some or all of the elements described above in relation to the computing device 1602. The one or more remote computers 1608 can include multiple computing devices, in various aspects. In aspects where the network 1606 is distributed in configuration, the one or more remote computers 1608 can be located at one or more different geographic locations. In an aspect where the one or more remote computers 1608 are a plurality of computing devices, each of the plurality of computing devices can be located across various locations such as buildings in a campus, medical and research facilities at a medical complex, offices or "branches" of a banking/credit entity, or can be mobile devices that are wearable or carried by personnel, or attached to vehicles or trackable items in a warehouse, for example. In some aspects, the remote computers 1608 are physically located in a medical setting such as, for example, a laboratory, inpatient room, an outpatient room, a hospital, a medical vehicle, a veterinary environment, an ambulatory setting, a medical billing office, a financial or administrative office, hospital administration setting, an in-home medical care environment, and/or medical professionals' offices. The remote computers 1608 might also be physically located in nontraditional healthcare environments so that the entire healthcare community might be capable of integration on the network 1606. In other aspects, the remote computers 1608 can be physically located in a non-medical setting, such as a packing and shipping facility or deployed within a fleet of delivery or courier vehicles.

Continuing, the computing environment 1600 includes a data store 1604. Although shown as a single component, the data store 1604 can be implemented using multiple data stores that are communicatively coupled to one another, independent of the geographic or physical location of a memory device. The data store 1604 can, for example, store data in the form of artifacts, server lists, properties associated with servers, environments, properties associated with environments, computer instructions encoded in multiple different computer programming languages, deployment scripts, applications, properties associated with applications, release packages, version information for release packages, build levels associated with applications, identifiers for applications, identifiers for release packages, users, roles associated with users, permissions associated with roles, workflows and steps in the workflows, clients, servers associated with clients, attributes associated with properties, audit information, and/or audit trails for workflows. The data store 1604 can, for example, also store data in the form of electronic records, such as electronic medical records of patients, patient-specific documents and historical records, transaction records, billing records, task and workflow records, chronological event records, and the like. Generally, the data store 1604 includes physical memory that is configured to store information encoded in data. For example, the data store 1604 can provide storage for computer-readable instructions, computer-executable instructions, data structures, data arrays, computer programs, applications, and other data that supports the functions and actions to be undertaken using the computing environment 1600 and components shown in the example of FIG. 16.

As shown in the example of FIG. 16, when the computing environment 1600 operates with distributed components that are communicatively coupled via the network 1606, computer instructions, applications, extensions, and/or program modules can be located in local and/or remote computer storage media (e.g., memory storage devices). Aspects of the present invention can be described in the context of computer-executable instructions, such as program modules, being executed by a computing device. Program modules can include, but are not limited to, routines, programs, objects, components, and data structures that perform particular tasks or implement particular abstract data types. In aspects, the computing device 1602 can access, retrieve, communicate, receive, and update information stored in the data store 1604, including program modules. Accordingly, the computing device 1602 can execute, using a processor, computer instructions stored in the data store 1604 in order to perform aspects described herein.

Although internal components of the devices in FIG. 16, such as the computing device 1602, are not illustrated, those of ordinary skill in the art will appreciate that internal components and their interconnection are present in the devices of FIG. 16. Accordingly, additional details concerning the internal construction device are not further disclosed herein. Although many other internal components of the computing device 1602 and the remote computers 1608 are not shown, such components and their interconnection are known. Accordingly, additional details concerning the internal construction of the computing device 1602 and the remote computers 1608 are not further disclosed herein.

Additionally, it will be understood by those of ordinary skill in the art that the computing environment 1600 is just one example of a suitable computing environment and is not intended to limit the scope of use or functionality of the present invention. Similarly, the computing environment 1600 should not be interpreted as imputing any dependency and/or any requirements with regard to each component and combination(s) of components illustrated in FIG. 16. It will be appreciated by those having ordinary skill in the art that the connections illustrated in FIG. 16 are just examples as other methods, hardware, software, and devices for establishing a communications link between the components, devices, systems, and entities can be utilized in implementation of the present invention. Although the connections are depicted using one or more solid lines, it will be understood by those having ordinary skill in the art that the example connections of FIG. 16 can be hardwired or wireless, and can use intermediary components that have been omitted or not included in FIG. 16 for simplicity's sake. As such, the absence of components from FIG. 16 should not be interpreted as limiting the present invention to exclude additional components and combination(s) of components. Moreover, though devices and components are represented in FIG. 16 as singular devices and components, it will be appreciated that some aspects can include a plurality of the devices and components such that FIG. 16 should not be considered as limiting the number of a device or component.

The present invention has now been described in relation to particular aspects, which are intended in all respects to be illustrative rather than restrictive. Thus the present invention is not limited to these aspects, but variations and modifications can be made without departing from the scope of the present invention.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

The invention claimed is:

1. A method for improved state identification and prediction in computerized queries, the method comprising:
   generating a model through word embedding;
   querying the model using a string to identify semantic matches;
   in response to querying the model, identifying a plurality of results comprising the semantic matches;
   determining probabilities for the plurality of results that represent semantic strength of the semantic matches;
   causing a ranked display of (a) the plurality of results comprising the semantic matches and (b) the probabilities determined for the plurality of results that represent semantic strength of the semantic matches in a graphical user interface (GUI);
   electronically aggregating data from a plurality of distinct workflows, the plurality of distinct workflows corresponding to a plurality of entities; and
   creating a probability table using the aggregated data, wherein the probability table includes a plurality of probabilities for a plurality of vectors, wherein the plurality of vectors correspond to preceding steps, current steps, and succeeding steps from the plurality of distinct workflows, and wherein each of the plurality of probabilities corresponds to a calculated likelihood of a preceding step and a succeeding step relative to a current step, for each step within each of the plurality of distinct workflows.

2. The method of claim 1, wherein generating the model through word embedding comprises:
   training a neural network model to create a plurality of multi-dimension document vectors, wherein each of the plurality of multi-dimension document vectors corresponds to a different workflow; and
   generating an index of the plurality of multi-dimension document vectors.

3. The method of claim 1, wherein generating the model through word embedding comprises:
   training a neural network model to create a plurality of multi-dimension document vectors, wherein each of the plurality of multi-dimension documents vectors corresponds to a step in a workflow; and
   generating an index of the multi-dimension document vectors.

4. The method of claim 1, wherein querying the model using a string to identify semantic matches comprises:
  determining to query a first model using the string, wherein the first model corresponds to a plurality of multi-dimension document vectors, wherein each of the plurality of multi-dimension document vectors corresponds to a step in a workflow; and
  generating a multi-dimension query vector of the string.

5. The method of claim 4, wherein identifying the one or more results comprises:
  determining a cosine similarity score between the query vector and the plurality of multi-dimension document vectors in an index of the first model; and
  selecting one or more of the plurality of multi-dimension document vectors from the index based on the cosine similarity score with the query vector, wherein the one or more selected multi-dimension document vectors are the one or more results.

6. The method of claim 1, wherein querying the model comprises:
  determining to query a first model using the string, wherein the first model corresponds to a plurality of multi-dimension document vectors, wherein each of the plurality of multi-dimension document vectors corresponds to a distinct workflow; and
  generating a multi-dimension query vector of the string.

7. The method of claim 6, wherein identifying the one or more results comprises:
  determining a cosine similarity score between the query vector and the plurality of multi-dimension document vectors in an index of the first model; and
  selecting one or more of the plurality of multi-dimension document vectors from the index based on the cosine similarity score with the query vector, wherein the one or more selected multi-dimension document vectors are the one or more results.

8. The method of claim 1, wherein the one or more results are displayed in a descending sequence based on a cosine similarity score ranging from +1 to −1, wherein +1 indicates increasing similarity relative to the string, and wherein −1 indicates decreased similarity relative to the string.

9. The method of claim 1, wherein generating the model through word embedding comprises transforming raw input data into a structured data set.

10. The method of claim 1, further comprising:
  generating a query vector of the query string; and
  querying the probability table to identify a first vector that is most similar to the query string vector, wherein the first vector corresponds to a preceding step or a current step.

11. The method of claim 10, further comprising:
  based on the first vector that is identified via querying, querying the probability table to identify a second vector having a highest probability of corresponding to a succeeding step for the preceding step or the current step of the first vector.

12. A non-transitory computer-readable storage medium having instructions embodied thereon, the instructions being executable by one or more processors to perform a method for improved state identification and prediction in computerized queries, the method comprising:
  generating a model through word embedding;
  searching the model using a query string to identify one or more semantic matches for the query string;
  in response to searching the model, identifying a plurality of results in the model, wherein the plurality of results comprising semantic matches between the query string and one or more of a step or workflow in the model;
  determining probabilities for the plurality of results that represent semantic strength of the semantic matches;
  predicting one or more additional results that are related to the plurality of results;
  causing a ranked display of (a) the plurality of results comprising semantic matches, (b) the probabilities for the plurality of results, and (c) the one or more additional results, in a graphical user interface (GUI);
  electronically aggregating data from a plurality of distinct workflows, the plurality of distinct workflows corresponding to a plurality of entities; and
  creating a probability table using the aggregated data, wherein the probability table includes a plurality of probabilities for a plurality of vectors, wherein the plurality of vectors correspond to preceding steps, current steps, and succeeding steps from the plurality of distinct workflows, and wherein each of the plurality of probabilities corresponds to a calculated likelihood of a preceding step and a succeeding step relative to a current step, for each step within each of the plurality of distinct workflows.

13. The non-transitory computer-readable storage medium of claim 12, wherein predicting one or more additional results that are related to the plurality of results comprises:
  using Markov chaining to identify a current step that corresponds to one of the plurality of results.

14. The non-transitory computer-readable storage medium of claim 12, wherein predicting one or more additional results that are related to the plurality of results comprises:
  using Markov chaining to identify, for one of the plurality of results, a current step and a preceding step, and to predict a succeeding step based on the current step and preceding step identified.

15. The non-transitory computer-readable storage medium of claim 12, wherein the method further comprises:
  generating a query vector of the query string; and
  querying the probability table to identify a first vector that is most similar to the query string vector, wherein the first vector corresponds to a preceding step or a current step.

16. The non-transitory computer-readable storage medium of claim 15, wherein the method further comprises:
  based on the first vector that is identified via querying, querying the probability table to identify a second vector having a highest probability of corresponding to a succeeding step for the preceding step or the current step of the first vector.

17. The non-transitory computer-readable storage medium of claim 12, wherein the method further comprises:
  training a neural network model to create a plurality of 500-dimension document vectors for steps, wherein each of the plurality of the 500-dimension document vectors corresponds to distinct steps;
  creating a first index of the plurality of the 500-dimension document vectors that corresponds to distinct work steps;
  training the neural network model to create the plurality of 500-dimension document vectors for workflows, wherein each of the plurality of the 500-dimension document vectors corresponds to distinct workflows; and creating a second index of the plurality of the 500-dimension document vectors that corresponds to distinct workflows.

18. The non-transitory computer-readable storage medium of claim 17, wherein querying the model comprises:
generating a 500-dimension query vector of the query string using the neural network model.

19. The non-transitory computer-readable storage medium of claim 18, wherein the method further comprises:
determining a cosine similarity score between the query vector and the plurality of 500-dimension document vectors in the first index or the second index.

20. The non-transitory computer-readable storage medium of claim 19, wherein the method further comprises:
selecting one or more of the plurality of 500-dimension document vectors from the first index or the second index based on the cosine similarity score with the query vector, wherein the one or more selected 500-dimension document vectors are provided as the one or more results.

21. A system for improved state identification and prediction in computerized queries, the system comprising:
one or more hardware processors that execute computer-readable instructions for a plurality of modules, the plurality of modules including:
a training module that generates a model through word embedding;
a query module that:
searches the model using a query string to identify one or more semantic matches for the query string;
in response to searching the model, identifies a plurality of results in the model, wherein the plurality of results correspond to semantic matches between the query string and one or more of a step or workflow in the model; and
determines probabilities for the plurality of results that represent semantic strength of the semantic matches;
a prediction module that predicts one or more additional results that are related to the plurality of results;
a display module that causes (a) a ranked display of the plurality of results comprising the semantic matches, (b) the probabilities determined for the plurality of results, and (c) the one or more additional results, in a graphical user interface (GUI); and
a module that:
electronically aggregates data from a plurality of distinct workflows, the plurality of distinct workflows corresponding to a plurality of entities; and
creates a probability table using the aggregated data, wherein the probability table includes a plurality of probabilities for a plurality of vectors, wherein the plurality of vectors correspond to preceding steps, current steps, and succeeding steps from the plurality of distinct workflows, and wherein each of the plurality of probabilities corresponds to a calculated likelihood of a preceding step and a succeeding step relative to a current step, for each step within each of the plurality of distinct workflows.

* * * * *